(12) United States Patent
Houser et al.

(10) Patent No.: US 8,394,115 B2
(45) Date of Patent: Mar. 12, 2013

(54) COMPOSITE END EFFECTOR FOR AN ULTRASONIC SURGICAL INSTRUMENT

(75) Inventors: Kevin L. Houser, Springboro, OH (US); Foster B. Stulen, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1452 days.

(21) Appl. No.: 11/386,399

(22) Filed: Mar. 22, 2006

(65) Prior Publication Data

US 2007/0225608 A1    Sep. 27, 2007

(51) Int. Cl.
*A61B 17/32* (2006.01)
(52) U.S. Cl. ............................................. 606/169
(58) Field of Classification Search .................. 606/169, 606/22, 27, 28, 40, 41, 49, 167, 170, 171, 606/174, 185
See application file for complete search history.

(56) References Cited

U.S. PATENT DOCUMENTS

| | | | |
|---|---|---|---|
| 4,827,911 A | 5/1989 | Broadwin et al. | |
| 5,046,854 A | 9/1991 | Weller et al. | |
| 5,449,370 A | 9/1995 | Vaitekunas | |
| 5,490,323 A | 2/1996 | Thacker et al. | |
| 6,241,703 B1 | 6/2001 | Levin et al. | |
| 6,254,623 B1 | 7/2001 | Haibel, Jr. et al. | |
| 6,277,084 B1 * | 8/2001 | Abele et al. | 601/2 |
| 6,325,808 B1 | 12/2001 | Bernard et al. | |
| 6,450,975 B1 * | 9/2002 | Brennan et al. | 600/585 |
| 6,454,781 B1 | 9/2002 | Witt et al. | |
| 6,589,253 B1 * | 7/2003 | Cornish et al. | 606/128 |
| 6,856,092 B2 | 2/2005 | Pothoven et al. | |
| 2001/0014801 A1 | 8/2001 | Tovey et al. | |
| 2001/0025183 A1 | 9/2001 | Shahidi | |
| 2002/0177843 A1 | 11/2002 | Anderson et al. | |
| 2004/0167496 A1 * | 8/2004 | Poole et al. | 604/529 |
| 2004/0176686 A1 * | 9/2004 | Hare et al. | 600/431 |
| 2004/0176751 A1 | 9/2004 | Weitzner et al. | |

FOREIGN PATENT DOCUMENTS

| | | |
|---|---|---|
| JP | 01-171537 | 7/1989 |
| JP | 05-095955 | 4/1993 |
| JP | 06-114069 | 4/1994 |
| JP | 07-136173 | 5/1995 |
| JP | 11-178834 | 7/1999 |
| JP | 11-192233 | 7/1999 |
| JP | 2002-085420 | 3/2002 |
| JP | 2004-208922 | 7/2004 |
| WO | 03/030754 | 4/2003 |
| WO | 2004/058074 | 7/2004 |
| WO | 2006/020943 | 2/2006 |

OTHER PUBLICATIONS

JP, Notification of Reasons for Refusal, Japanese Application No. 2007-072907 (Mar. 6, 2012).
AU, Examiner's First Report, Australian Application No. 2007201176 (Feb. 3, 2012).
EP, Search Report, European Application No. 07251201.5 (Jul. 17, 2007).
EP, Examination Report, European Application No. 07251201.5 (Dec. 18, 2008).
EP, Decision to Grant, European Application No. 07251201.5 (Apr. 21, 2011).

* cited by examiner

*Primary Examiner* — Kathleen Sonnett
*Assistant Examiner* — Jocelin Tanner

(57) ABSTRACT

A composite end effector for an ultrasonic surgical instrument is provided and includes a first portion formed from a first material that exhibits a first characteristic value when excited by an ultrasonic energy input and a second portion formed from a second material that exhibits a second characteristic value when excited by the ultrasonic energy input. The composite end effector exhibits a composite characteristic value different from the first and second characteristic values when excited by the ultrasonic energy input.

15 Claims, 6 Drawing Sheets

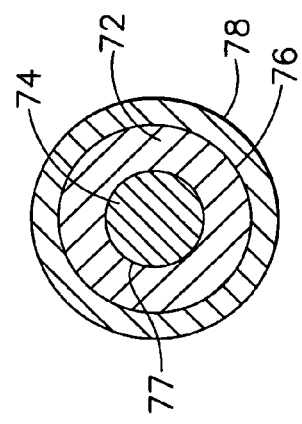
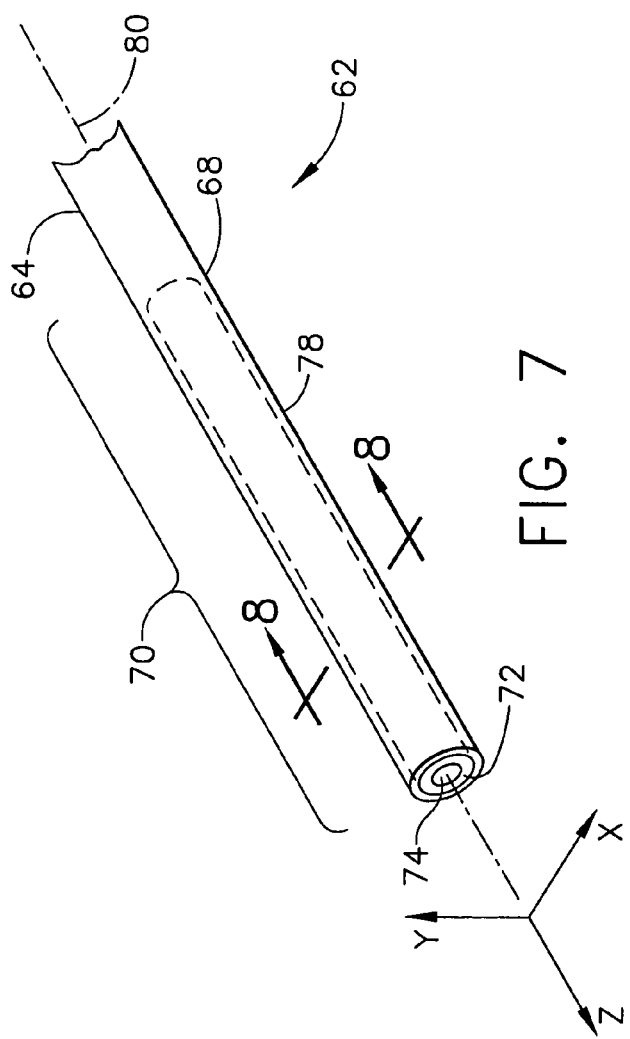

COMPOSITE END EFFECTOR FOR AN ULTRASONIC SURGICAL INSTRUMENT

FIELD OF THE INVENTION

Background of the Invention

The present application relates to ultrasonic surgical instruments and, more particularly, to ultrasonic surgical instruments having end effectors for cutting and coagulating tissue.

Surgeons use ultrasonic instruments in surgery to cut and coagulate tissue. Piezoelectric elements are electrically excited at a resonant frequency of an ultrasonic instrument to create vibrations that are transmitted through a resonator and amplified to produce a mechanical, standing wave vibration of the same frequency. An ultrasonic transmission assembly of the instrument has an elongated, transmission waveguide that transmits this vibration to an end effector (e.g., cutting blade) on the distal tip of the instrument. The end effector may vibrate primarily in the longitudinal direction to generate localized heat within adjacent tissue, although some instruments have been designed specifically so that the end effector vibrates primarily in either of the transverse (perpendicular to the longitudinal axis) or torsional (about the longitudinal axis) directions to treat tissue.

The distal tip of the end effector corresponds to a vibratory anti-nodal point. The proximal end of the end effector typically attaches to the waveguide slightly distal to the most distal, vibratory nodal point of the ultrasonic transmission assembly. This arrangement allows tuning of the instrument to a preferred resonant frequency when the end effector is not loaded with tissue. By definition, therefore, the length of the end effector is slightly less than one-quarter of the acoustic wavelength that propagates through the end effector material when excited by an ultrasonic energy input of a particular frequency.

Ultrasonic surgical end effectors formed from different materials may exhibit significantly different acoustical and mechanical characteristics. These characteristics may be associated with material properties such as ultrasonic propagation wavelength, conductive heat transfer, mechanical fatigue strength and acoustic transmission efficiency. For example, an end effector formed from a material such as a ceramic having a relatively high ratio of elastic modulus to density may have a longer ultrasonic propagation wavelength than that of an end effector formed from a material such as a metal having a relatively low ratio.

End effectors of some current ultrasonic surgical instruments are made of a Ti-6Al-4V titanium alloy. The ultrasonic propagation wavelength of the titanium alloy is about 87 mm when operated at an ultrasonic frequency of 55.5 kHz, so that the length of the end effector is about 22 mm. For certain surgical applications the surgeon may prefer a slightly longer end effector than what is currently available.

The acoustic wavelength in a material is equal to the speed of sound in the material divided by the frequency (cycles/sec.) of the ultrasonic energy input. Therefore, one way to provide instruments with longer end effectors is to decrease the frequency of the ultrasonic energy input. For example, reducing the frequency from approximately 55.5 kHz to approximately 27.8 kHz increases the characteristic wavelength in a titanium alloy to approximately 174 mm. However, there is a practical lower limit to excitation frequency. An end effector vibrating near 22 kHz may create a painfully audible sound to humans and obviously would not be desirable in a surgical operating room.

Another way to provide instruments with longer end effectors is to select end effector materials in which sound travels faster. The speed of sound in a material is a function of material density and modulus of elasticity. Basically, materials having a high elastic modulus to density ratio propagate ultrasonic energy faster than materials having a relatively low ratio. Certain ceramic materials, including alumina ($Al_2O_3$), exhibit characteristic wavelengths that are approximately twice as great as some titanium alloys. Unfortunately, ceramic materials are very brittle and ceramic end effectors would be susceptible to breakage during normal handling, set-up and operation.

In addition to providing longer end effectors, it may be desired to improve the acoustical transmission efficiency of the end effector in order to reduce "self-heating" of the end effector and the time to cut and coagulate tissue. Some materials such as sapphire, titanium and aluminum may transmit ultrasonic energy more efficiently than other materials such as copper and steel. Acoustical transmission efficiency of surgical ultrasonic end effectors may be associated with a unitless acoustical coefficient, known in the art as the "Q" coefficient, which for the Ti-6Al-4V titanium alloy and some aluminum alloys is in the range of 10,000 to 20,000. The Q coefficient for certain steels may be as low as 250. For applications in which self-heating of the end effector should be minimized, the end effector may be formed from a material having a high Q coefficient. However, there may be some surgical applications in which rapid self-heating of the end effector is desired, such as when the end effector is used while immersed in body fluids. For such applications, the end effector may be formed from a material having a lower Q coefficient in order to quickly generate heat in the tissue to cut and coagulate the tissue.

The thermal conductivity of the end effector material may also significantly affect how quickly the end effector cuts and coagulates tissue. If the end effector conducts heat to the tissue too quickly, the tissue may char. But if the end effector conducts heat to the tissue too slowly, the device may cut and/or coagulate too slowly. Depending on the surgical application, an end effector formed from the Ti-6Al-4V alloy, which has a thermal conductivity of about 7 W/m-K, may retain too much heat, whereas an end effector formed from aluminum, which has a thermal conductivity of about 200 W/m-K, may pull too much heat away from the tissue.

The mechanical fatigue strength of the end effector material may significantly affect the operational life of the end effector and, consequently, how many times the end effector can be used during a surgical procedure. Fatigue strength is sometimes referred to as the endurance limit of the material and corresponds to the stress at which the material may be reversibly stressed for practically an infinite number of cycles. The Ti-6Al-4V alloy has a fatigue strength of about 413 kPa, whereas the fatigue strength of aluminum is about 138 kPa. Aluminum also is softer than the titanium alloy and is more easily damaged by other surgical instruments during usage, possibly leading to crack initiation that may further reduce the fatigue resistance of the end effector.

Clearly, the design of surgical ultrasonic end effectors has been very challenging at least in part because the available choices for a single end effector material that has the combination of acoustical and mechanical characteristics desired for certain surgical applications is very limited. For example, it may be desired to provide a surgical ultrasonic end effector that has a longer ultrasonic propagation wavelength and a greater fatigue strength than current end effectors, and yet maintains the acoustic efficiency and thermal characteristics of current end effectors.

Accordingly, there is a need for a surgical ultrasonic end effector that exhibits a combination of certain desired acoustical and/or mechanical characteristics that may not be provided by a conventional end effector formed from a single material.

SUMMARY OF THE INVENTION

In one embodiment, a composite end effector for an ultrasonic surgical instrument has a first portion formed from a first material that exhibits a first characteristic value when excited by an ultrasonic energy input and a second portion formed from a second material that exhibits a second characteristic value when excited by the ultrasonic energy input. The composite end effector exhibits a composite characteristic value different from the first and second characteristic values when excited by the ultrasonic energy input.

In another embodiment, a composite end effector for use with an ultrasonic surgical instrument has a plurality of portions, wherein each portion is formed from one of a plurality of materials, and wherein each material exhibits a characteristic value when excited by an ultrasonic energy input, and wherein the composite end effector exhibits a composite characteristic value different from any one of the characteristic values when excited by the ultrasonic energy input.

In another embodiment, a composite end effector for an ultrasonic surgical instrument has a plurality of portions formed from a material and joined together such that the composite end effector exhibits an enhanced resistance to fracture propagation through the end effector when excited by the ultrasonic energy input. At least one of the portions is a laminated portion joined to an adjacent portion such that a fracture initiated in the laminated portion does not propagate through the adjacent portion.

Other embodiments of the composite end effector will become apparent from the following description, the accompanying drawings and the appended claims.

BRIEF DESCRIPTION OF THE FIGURES

FIG. 7 is a perspective view of a third embodiment of an end effector attached to the distal end of a transmission waveguide;

FIG. 8 is a cross sectional view taken at line 8-8 of the end effector shown in FIG. 7;

DETAILED DESCRIPTION OF THE INVENTION

Figure 1:
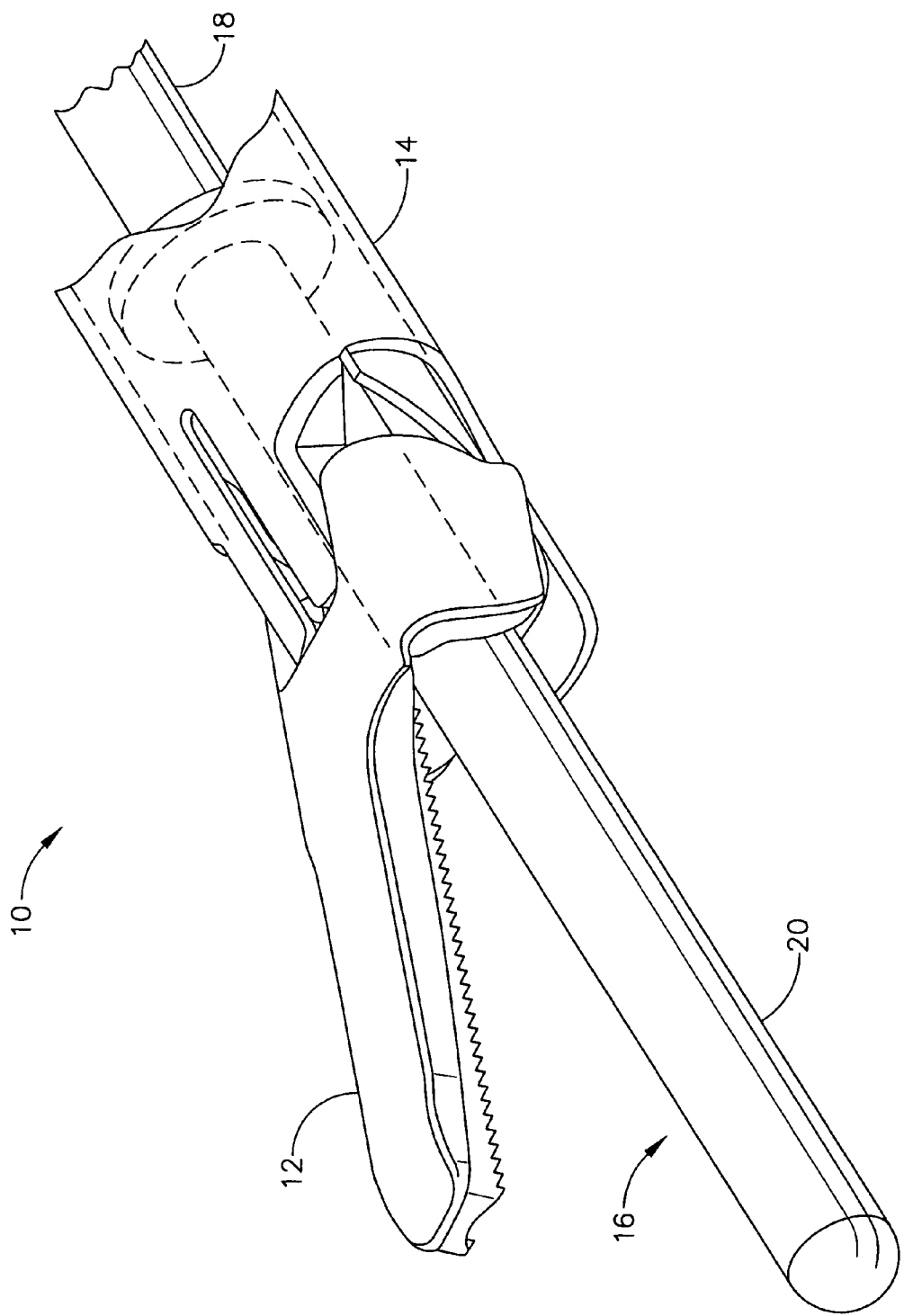
FIG. 1 is a perspective view of the distal portion of an ultrasonic surgical instrument of the prior art.

FIG. 1 is a perspective view of the distal portion of an ultrasonic surgical instrument of the prior art, generally designated 10. Ultrasonic surgical instrument 10 is also referred to as an ultrasonic clamp coagulator apparatus, and is disclosed in U.S. Pat. No. 6,254,623, issued to Haibel, et. al. on Jul. 3, 2001. Ultrasonic surgical instrument 10 is one example of numerous ultrasonic surgical instruments that may be improved for certain surgical procedures by providing a composite end effector as described herein. Ultrasonic surgical instrument 10 may be operatively connected to a handheld, ultrasonic drive unit that is powered by an ultrasonic generator (not shown). Ultrasonic surgical instrument 10 includes an ultrasonic transmission assembly 16 that has an elongated, transmission waveguide 18. Waveguide 18 may be semi-flexible or substantially rigid. Waveguide 18 amplifies and transmits vibrations from the ultrasonic drive unit to an end effector 20, as is well-known in the art. The distal tip of end effector 20 may vibrate in the longitudinal direction with a peak-to-peak amplitude of approximately 10-200 microns at an ultrasonic frequency of 55.5 kHz. An elongated sheath 14 retains waveguide 18 and the proximal end of end effector 16. A clamp arm 12 pivotally attaches to the distal end of sheath 14. A surgeon may remotely operate clamp arm 12 to hold tissue against end effector 20 while energizing end effector 20 in order to cut and/or coagulate the tissue.

End effector 20 and waveguide 18 may be unitarily formed from a titanium alloy such as Ti-6Al-4V, an aluminum alloy, or from any other suitable material. Alternately, end effector 20 may be formed separately from the same material as waveguide 18, or from an alternate material. End effector 20 then may be attached to waveguide 18 by a threaded connection or by a welded joint, for example. As is well-known in the art, the proximal end of end effector 20 may be located near the most distal, vibratory nodal point of waveguide 18. The distal end of end effector 20 corresponds to the location of a vibratory anti-nodal point. The length of end effector 20, therefore, is approximately equal to one quarter of the acoustic wavelength that is characteristic of the material composition of the end effector for a particular ultrasonic energy input frequency. For example, when end effector 20 is formed from Ti-6Al-4V, the characteristic wavelength is approximately 87 mm, and the length of end effector 20 is approximately 22 mm.

Figure 3:
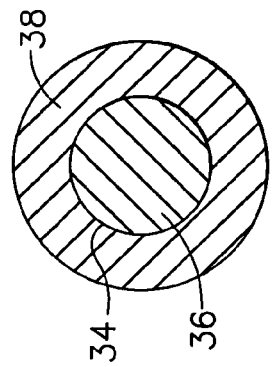
FIG. 3 is a cross sectional view taken at line 3-3 of the end effector shown in FIG. 2.
Figure 2:
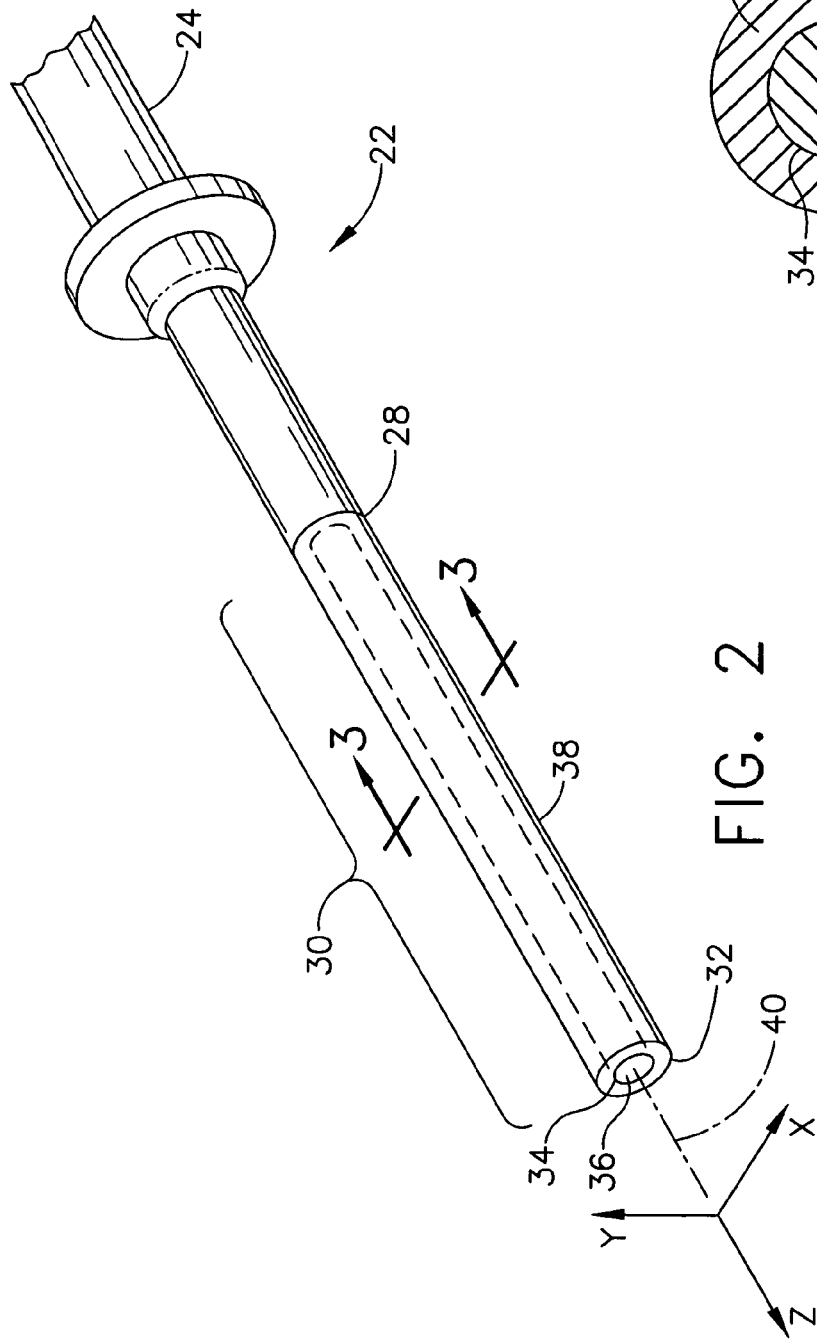
FIG. 2 is a perspective view of a first embodiment of an end effector attached to the distal end of a transmission waveguide.

FIG. 2 is a perspective view of the distal portion of a first embodiment of an ultrasonic transmission assembly 22 for an ultrasonic surgical instrument. FIG. 3 is a cross-sectional view of assembly 22 taken at line 3-3 of FIG. 2. Assembly 22 includes a waveguide 24 that may be similar to the prior art waveguide 18 shown in FIG. 1. The distal end of waveguide 24 attaches to the proximal end of a composite end effector 30 near a first vibratory nodal point 28. Nodal point 28 may also be positioned slightly proximal to the proximal end of end effector 30. The ordinate system shown in FIG. 2 defines a longitudinal axis 40 of assembly 22 to be parallel to the z-axis. Composite end effector 30 includes a cylindrical, first portion 38 having a circular cross-section. First portion 38 has a bore 34 (also referred to as a cavity) coaxial to longitudinal axis 40 and extending between the distal and proximal ends of end effector 30. A cylindrical, second portion 36 may be positioned inside of bore 34 and may substantially fill bore 34. It should be noted that although the bore 34 in the first portion 38 is shown to extend to near a vibratory nodal point 28, alternative aspects of this approach allow for the bore 34 to extend a fraction of single or multiple wavelengths through the material, up to and including through the entire waveguide 24.

First portion 38 may be formed from a first material, which may be any one of a number of suitable materials, including a titanium alloy such as Ti-6Al-4V and an aluminum alloy such as 7075-T6. First portion 38 provides a relatively tough, outer covering to second portion 36 to resist structural stresses during normal handling, set-up and operation of the ultrasonic surgical instrument. First portion 38 characteristically (wherein "characteristically" refers to the acoustic properties normally exhibited by the material) vibrates, for example, with a first wavelength when excited by an ultrasonic energy input, such as may be provided by the ultrasonic drive unit of the ultrasonic surgical instrument. An example of an ultrasonic energy input is approximately 3 watts at a frequency of about 55.5 kHz. An example of a first wavelength is approximately 87 mm.

Second portion 36 is formed from a second material, which may be any one of a number of suitable materials, including alumina, aluminum nitride, zirconia, silicon carbide, silicone nitride, sapphire and ruby. Second portion 36 may extend only a portion or the entire length of end effector 30. Second portion 36 characteristically vibrates, for example, with a second wavelength when separately excited by the ultrasonic energy input. The second wavelength may be substantially greater than the first wavelength of first portion 38. An example of a second wavelength is approximately 174 mm.

First portion 38 and second portion 36 may be joined together using any one or a combination of a number of well-known processes, including but not limited to, brazing, fritting and mechanically coupling. When first portion 38 and second portion 36 are joined together and excited by the ultrasonic energy input, composite end effector 30 characteristically vibrates with a composite wavelength that is between the first and second wavelengths. For example, if the first wavelength of first portion 38 is approximately 87 mm and the second wavelength of second portion 36 is approximately 174 mm, a composite wavelength may fall in the range of approximately 87 to 174 mm. In addition to the materials used for first portion 38 and second portion 36, the exact magnitude of the composite wavelength may depend upon other factors, including physical configuration, mass proportion and distribution and the strength of the bond between first portion 38 and second portion 36.

Similarly, one or more of other material properties, including thermal conductivity, coefficient of friction (i.e., how the material interacts with tissue), ultrasonic power transmission efficiency and fatigue strength of end effector 30 may have composite characteristic values, although not necessarily. Furthermore, each composite characteristic value associated with a material property may be in a range defined by the characteristic values for that material property of first portion 38 and second portion 36.

Composite end effector 30 may be configured such that its proximal end is near the most distal, vibrational nodal point 28 of waveguide 24, and such that the length of composite end effector 30 is approximately equal to a quarter of the composite wavelength. Therefore, the length of composite end effector 30 may be significantly longer than the length of a similarly configured and ultrasonically energized end effector made only of a single material such as a titanium alloy.

As shown in FIG. 2, second portion 36 may have a uniform diameter along its entire length. First portion 38 and second portion 36 may be joined together with a tight bond and with minimal gaps in the entire area between the interfacing surfaces to ensure consistently optimal performance of composite end effector 30. A method for making composite end effector 30 may include providing a first rod formed from a first material such as a titanium alloy and creating a longitudinal bore extending between the proximal and distal ends of the first rod, such as by a drilling process. For example, the first rod may have an outer diameter of about five millimeters and the longitudinal bore may have a diameter of about four millimeters. The method may further include providing a second rod formed from a second material, such as man-made sapphire, and sizing the diameter of the second rod to fit tightly inside the longitudinal bore of the first rod. The method may further include joining the first rod to the second rod by a joining process. The joining process may be, for example, a fritting process, a brazing process, a mechanical process or a combination of such processes.

Fritting and brazing processes are well-known in the cardiac pacemaker industry for making biocompatible, hermetically-sealed, long-lasting, electrical lead "feed-throughs" through the pacemaker housing. Fritting processes include a ceramic-to-metal sealing process that may be used to bond a ceramic, such as 95% alumina or 100% alumina (sapphire), to a metal, such as titanium, stainless steel or molybdenum. The ceramic (such as second portion 36 of end effector 30 in FIG. 2) may be metalized using a powder refractory metal or a thin film sputtered metalizing technique. The metalized ceramic may then be held with high pressure to the metal (such as first portion 38 of end effector 30 in FIG. 2) and subjected to high heat for a period of time to bond the ceramic and metal together.

It is also possible to braze second portion 36 and first portion 38 together with a brazing alloy (e.g., silver, gold or gold-copper), although such brazing alloys are generally "lossy" (i.e., they do not propagate acoustic energy efficiently and tend to rapidly generate heat) in regards to propagation of an ultrasonic energy input. However, the use of lossy materials in the composition of end effector 30, including the forming of second portion 36 from a lossy material such as silver, gold, and the like, would potentially allow end effector 30 to be particularly suitable for use in a fluidic environment. For example, surgeons often use ultrasonic surgical instruments to cut and/or coagulate tissue submerged in body fluids that rapidly dissipate heat from the end effector. Consequently, the time required to cut and/or coagulate tissue is significantly increased, which may be very costly to the patient. Ultrasonic instruments having end effectors composed of lossy materials and specifically adapted to cut and coagulate tissue even when the end effector is submerged in a body fluid may be provided for such surgical procedures.

Second portion 36 may also be formed from a second material that is an excellent heat conductor, such as an aluminum alloy. Heat generated in the tissue during operation may be rapidly conducted to waveguide 24, which may act as a heat sink, thereby helping to prevent overheating and prolonging the life of end effector 30.

First portion 38 and second portion 36 may be formed from the same material, such as a titanium alloy. Such a version of end effector 30 would retain the acoustic properties characteristic of the selected material and also be more resistant to crack propagation failures originating from a material defect or "nick" on the surface of first portion 38.

Mechanically joining or coupling second portion 36 to first portion 38 may include press fitting second portion 36 into bore 34 of first portion 38 or mechanically compressing first portion 38 onto second portion 36. Alternately, a thermal process may be used, for example, in which first portion 38 is heated to increase the diameter of bore 34 before positioning second portion 36 into bore 34. The assembly may then be permitted to cool so that first portion 38 contracts tightly onto second portion 36. Various other well-known mechanical processes may also be used, as is apparent to those skilled in the art.

Figure 6:
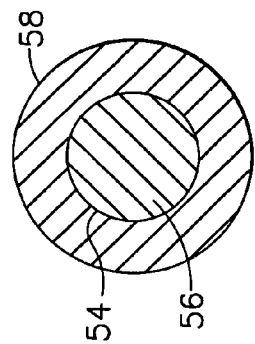
FIG. 6 is a cross sectional view taken at line 6-6 of the end effector shown in FIG. 4.
Figure 5:
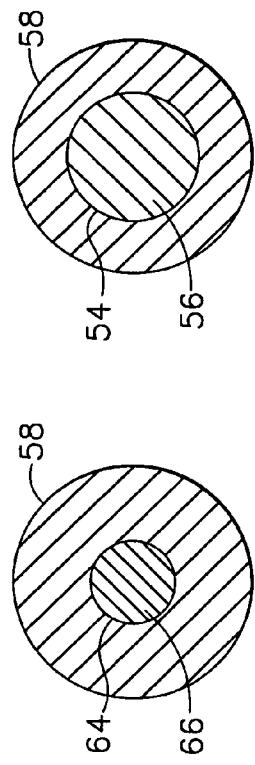
FIG. 5 is a cross sectional view taken at line 5-5 of the end effector shown in FIG. 4.
Figure 4:
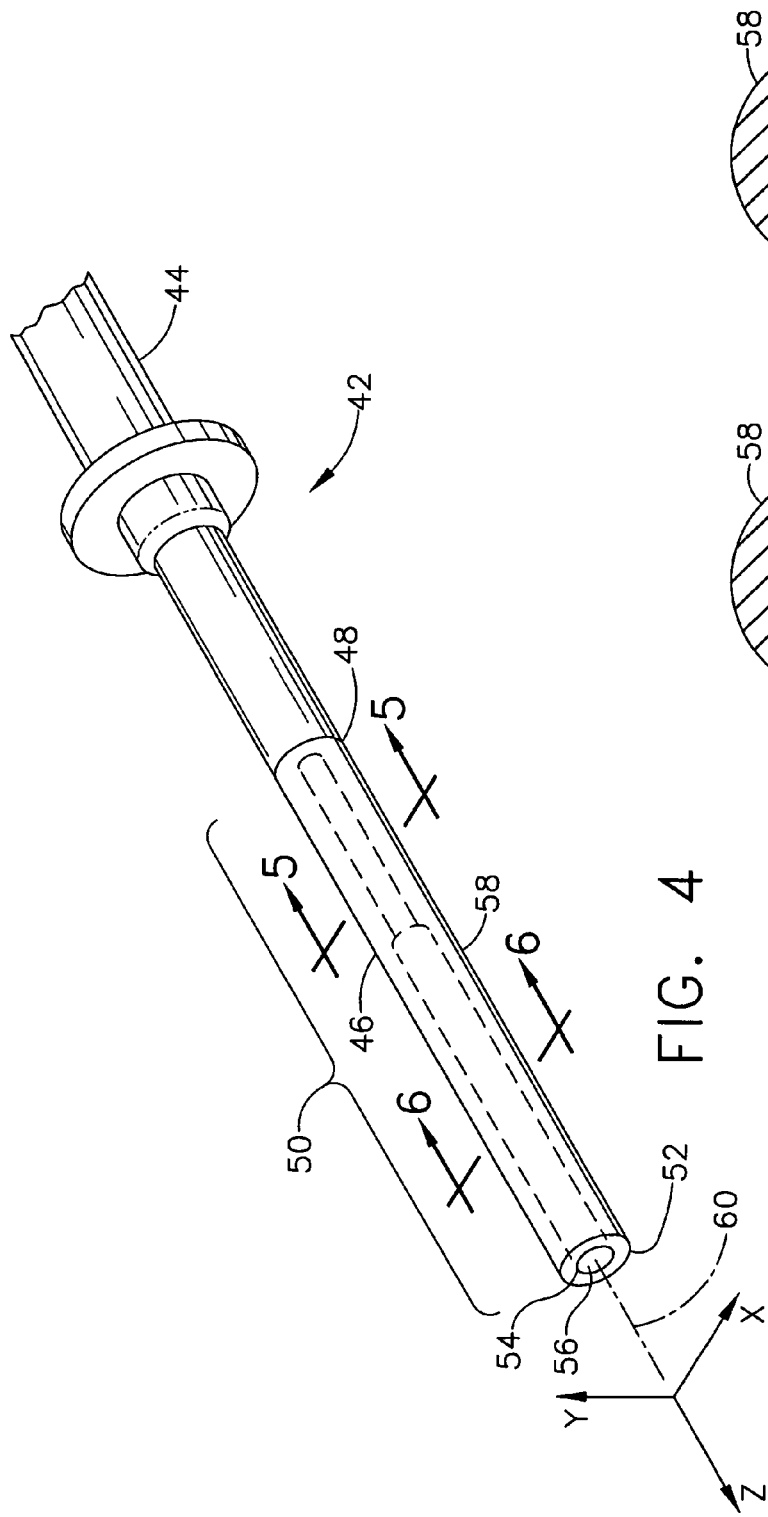
FIG. 4 is a perspective view of a second embodiment of an end effector attached to the distal end of a transmission waveguide.

FIG. 4 is a perspective view of the distal portion of a second embodiment of an ultrasonic transmission assembly 42 for an ultrasonic surgical instrument. FIG. 5 is a cross-sectional view of assembly 42 taken at line 5-5 of FIG. 4. FIG. 6 is a cross-sectional view of assembly 42 taken at line 6-6 of FIG. 4. Assembly 42 may include a waveguide 44 that may be similar to the prior art waveguide 18 shown in FIG. 1. The distal end of waveguide 44 may attach to the proximal end of a composite end effector 50 near a first vibratory nodal point 48. The ordinate system shown in FIG. 4 defines a longitudinal axis 60 of assembly 42 to be parallel to the z-axis. Composite end effector 50 may include a cylindrical, first portion 58 having a circular cross-section. First portion 58 may have a first bore 54 coaxial to longitudinal axis 60 and extending between the distal end and an intermediate point 46 of end effector 50. First portion 58 also may have a second bore 64 coaxial to longitudinal axis 60 and extending between intermediate point 46 and the proximal end of composite end effector 50. A cylindrical, second portion 56 may be positioned inside of first bore 54 and may substantially fill first bore 54. A cylindrical, third portion 66 may be positioned inside of second bore 64 and may substantially fill second bore 64.

First portion 58 may be formed from a first material, which may be any one of a number of suitable materials, including a titanium alloy, such as Ti-6Al-4V, and an aluminum alloy such as 7075-T6. First portion 58 provides a relatively tough, outer covering to second portion 56 and third portion 66. First portion 58 characteristically vibrates with a first wavelength when excited by an ultrasonic energy input. Second portion 56 may be formed from a second material, which may be any one of a number of suitable materials, including alumina, aluminum nitride, zirconia, silicon carbide, silicone nitride, sapphire and ruby. Second portion 56 characteristically vibrates with a second wavelength when excited by the ultrasonic energy input. Third portion 66 may be formed from a third material, which may be any one of a number of suitable materials, including alumina, aluminum nitride, zirconia, silicon carbide, silicone nitride, sapphire and ruby. Third portion 66 characteristically vibrates with a third wavelength when excited by the ultrasonic energy input.

First portion 58, second portion 56 and third portion 66 may be joined together using any one of a number of well-known processes, including but not limited to brazing, fritting and mechanically coupling. Composite end effector 50 characteristically vibrates with a composite wavelength that is in a range bounded by the highest and lowest of the first, second and third wavelengths.

Composite end effector 50 may be configured such that its proximal end is near the most distal vibratory nodal point 48 of waveguide 44 and that its length is approximately equal to a quarter of the composite wavelength. Therefore, the length of composite end effector 50 may be significantly longer than the length of a similarly configured and ultrasonically energized end effector made only of a single material such as a titanium alloy.

As shown in FIGS. 5 and 6, the diameter of third portion 66 may be smaller than the diameter of second portion 56. This arrangement may be desired so that end effector 50 is sufficiently resistant to structural stresses occurring at the transition between waveguide 44 and end effector 50. Alternately, the diameter of third portion 66 may also be the same or larger than the diameter of second portion 56. Also, the third material of third portion 66 may be the same or different than the second material of second portion 56.

The lengths of second portion 56 and third portion 66 may vary. The combined lengths of second portion 56 and third portion 66 may be approximately equal to or less than the length of end effector 50.

FIG. 7 is a perspective view of the distal portion of a third embodiment of an ultrasonic transmission assembly 62 for an ultrasonic surgical instrument. FIG. 8 is a cross-sectional view of assembly 62 taken at line 8-8 of FIG. 7. Assembly 62 may include a waveguide 64 that may be similar to the prior art waveguide 18 shown in FIG. 1. The distal end of waveguide 64 may attach to the proximal end of a composite end effector 70 near a first vibratory nodal point 68. The ordinate system shown in FIG. 7 defines a longitudinal axis 80 of assembly 62 to be parallel to the z-axis. Composite end effector 70 may include a first portion 78 made of a first material, a second portion 72 made of a second material and a third portion 74 made of a third material. The three portions may be coaxially arranged about longitudinal axis 80 and joined together using any one or more of the joining processes previously described herein. The first, second and third materials characteristically exhibit a first, second and third acoustic wavelength, respectively, when excited by an ultrasonic energy input. The first, second and third materials may include any combination of materials selected from the same materials previously described for the first and second embodiments. First portion 78 may have a round cylindrical shape with a first bore 76 extending the entire length of composite end effector 70, and may retain second portion 72. Second portion 72 may have a round cylindrical shape with a second bore 77 extending the entire length of composite end effector 70, and may retain third portion 74. Third portion 74 may be a rod that substantially fills second bore 77. End effector 70 may have a composite wavelength in a range bounded by the lowest and highest of the first, second and third wavelengths.

Second portion 72 may also be formed from a tubular material such that second portion 72 defines a channel or chamber and third portion 74 is formed from a fluid such as air, another gas or a liquid contained in the channel or chamber. Second and third portions 72, 74 may extend the entire length or only a portion of the length of end effector 70.

Those skilled in the art will recognize that a composite end effector may include a plurality of portions, wherein each portion may have any one of a number of configurations, and the portions may be joined together in any one of a number of arrangements. Each portion may be made of a material that is the same or different than the material of any other portion. Therefore, it is possible to provide a composite end effector with a desired combination of characteristics related to, but not limited to, composite wavelength when excited by an ultrasonic energy input, structural strength, configuration (including length), mass distribution, manufacturing cost, operating life, heat conduction and heat generation. Each portion may be formed from one of a plurality of materials, wherein each material exhibits a characteristic value of a material property when excited by an ultrasonic energy input, and wherein the composite end effector exhibits a composite characteristic value different from any one of the characteristic values of each material when excited by the ultrasonic energy input.

It is also possible to provide a composite end effector for an ultrasonic surgical instrument having a plurality of portions formed from a material and joined together such that the composite end effector exhibits an enhanced resistance to fracture propagation through the end effector when excited by the ultrasonic energy input. At least one of the portions may be a laminated portion joined to an adjacent portion such that a fracture initiated in the laminated portion does not propagate through the adjacent portion.

For example, each of concentric portions 72, 74 and 78 of end effector 70 shown in FIG. 7 may be formed from a titanium alloy (such as Ti-6Al-4V) and joined such that a fracture initiated in first (outer) portion 78 would not propagate into the adjacent portion 72, thereby prolonging the operational life of end effector 70. Fractures are likely to initiate in first portion 78 due to damage from other surgical instruments. Since first portion 78 is a relatively small portion of end effector 70, being cracked may not create enough impedance to disable end effector 70. In this way, end effector 70 may be more robust than a non-laminated end effector in its ability to absorb damage without becoming non-functional.

Figure 9:
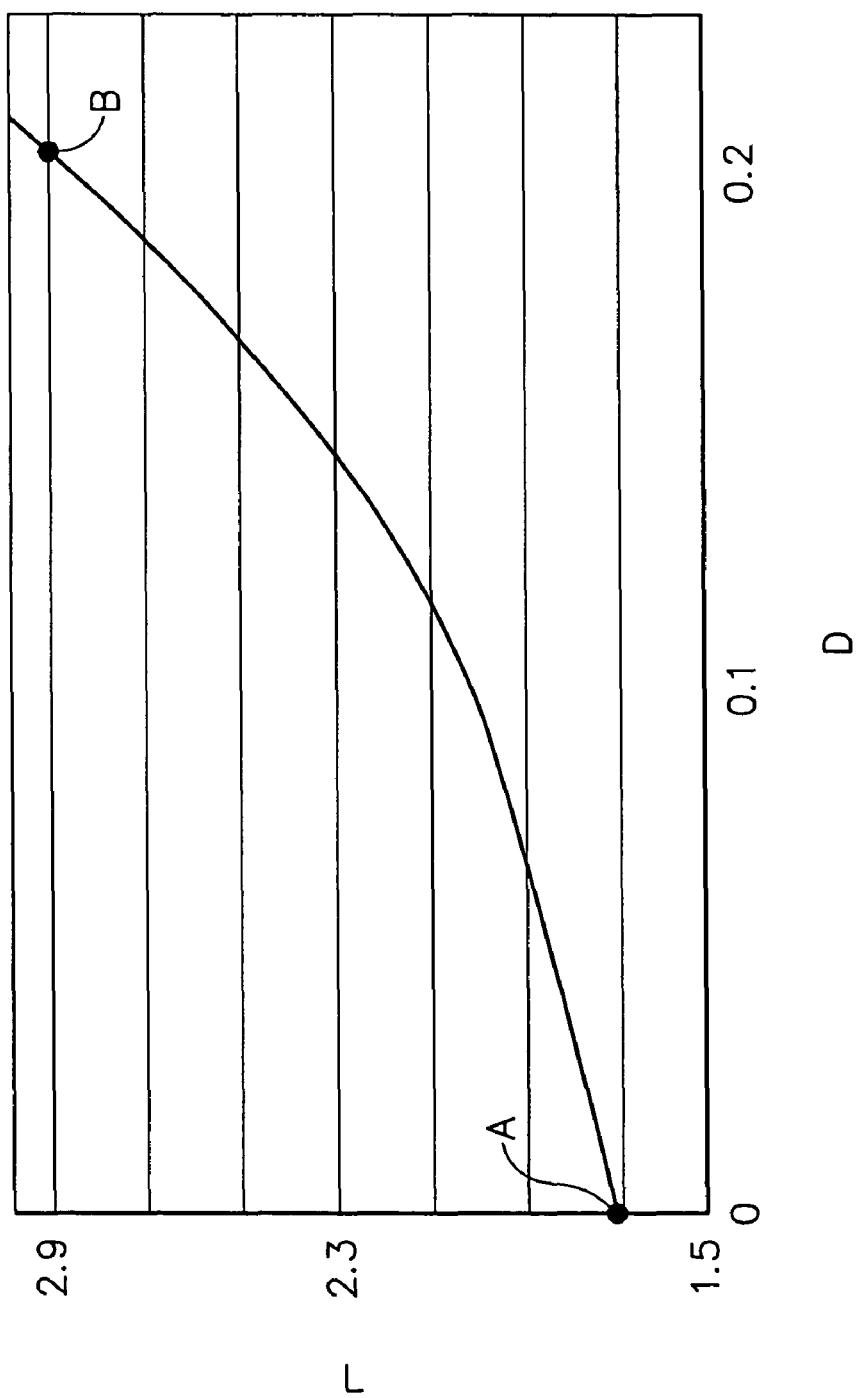
FIG. 9 is a graph showing the results of an analysis using a mathematical model of a composite end effector formed from a titanium alloy and an alumina ceramic, wherein D denotes a diameter of the alumina ceramic, and L denotes one-half of the composite wavelength (inches) when the composite end effector is excited by an ultrasonic energy input.

Composite end effectors such as disclosed herein may be modeled using finite element analysis techniques to estimate the composite wavelength. FIG. 9 is a graph showing the results of an analysis using a mathematical model of a composite end effector similar to end effector 30 of FIG. 2. In the model, the composite end effector has a cylindrical, outer portion made of a titanium alloy such as Ti-6Al-4V and having a longitudinal bore along its entire length. The outer portion has an outer diameter of 6.35 mm. A 100% alumina ceramic (sapphire) rod completely fills the bore and is assumed to be "perfectly" attached to the titanium alloy. "D" denotes a diameter of the alumina ceramic rod. "L" denotes one half of the composite wavelength (inches) predicted by the model when the composite end effector is excited by an ultrasonic energy input having a frequency of 55.5 kHz.

As the mathematical model shown in FIG. 9 illustrates, when the diameter of the second portion is approximately zero at the point indicated by the letter "A", the half-wavelength is predicted to be approximately 44 mm. This corresponds to when the end effector is formed entirely from the first material (titanium alloy). When the diameter of the second portion is approximately 5 mm at the point indicated by the letter "B", the half-wavelength is predicted to be approximately 74 mm. This corresponds to when only a very thin titanium alloy shell covers the sapphire core.

It is possible to develop more sophisticated mathematical models for predicting the composite wavelengths of composite end effectors having a plurality of portions formed from a plurality of materials. These mathematical models may be further developed and refined by performing iterative tests of physical models.

Figure 10:
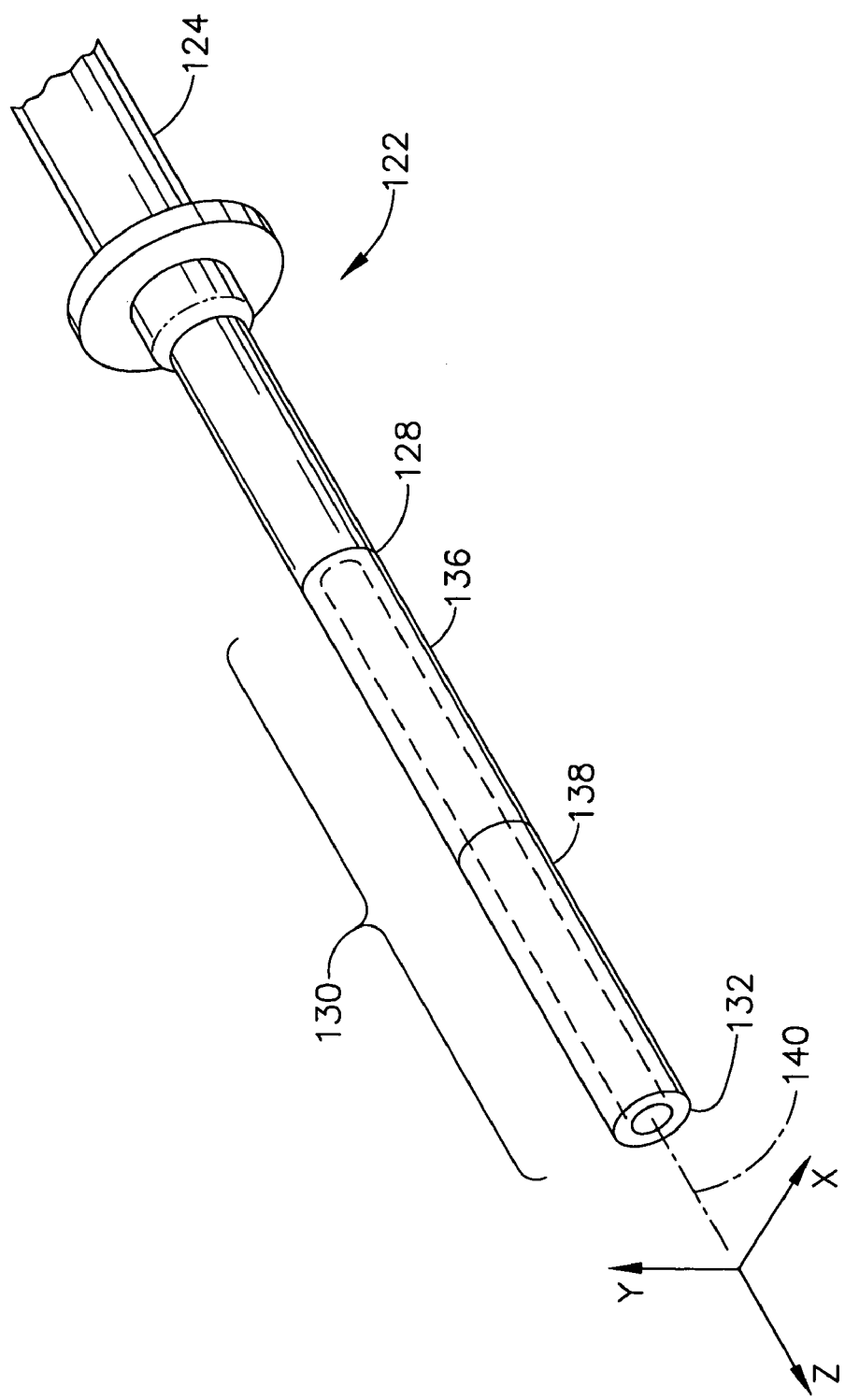
FIG. 10 is a front perspective view of an alternative aspect of the device shown in FIG. 2.

FIG. 10 is an alternative aspect of the device shown in FIG. 2 wherein the ultrasonic transmission assembly 122 is made up of a waveguide 124 having a distal end attached to the proximal end of a composite end effector 130 near a first vibratory nodal point 128. Nodal point 128 may also be positioned slightly proximal to the proximal end of end effector 130. The ordinate system shown in FIG. 10 defines a longitudinal axis 140 of assembly 122 to be parallel to the z-axis. Composite end effector 130 may include a cylindrical, first portion 136 and a second portion 138 both having a circular cross-section, although any cross-section may be suitable. Additionally, each portion may also have a circular bore filled with a third portion not shown in a manner similar to that described above.

First portion 136 may be formed from a first material, which may be any one of a number of suitable materials, including a titanium alloy such as Ti-6Al-4V, an aluminum alloy such as 7075-T6, alumina, aluminum nitride, zirconia, silicon carbide, silicone nitride, sapphire and ruby selected for one or more material properties, including, but not limited to speed of sound, thermal conductivity, ultrasonic power transmission efficiency, coefficient of friction and fatigue strength. First portion 136 characteristically (wherein "characteristically" refers to the acoustic properties normally exhibited by the material) vibrates, for example, with a first wavelength when excited by an ultrasonic energy input, such as may be provided by the ultrasonic drive unit of the ultrasonic surgical instrument. An example of an ultrasonic energy input is approximately 3 watts at a frequency of about 55.5 kHz. An example of a first wavelength is approximately 87 mm.

Second portion 138 may be formed from a second material, which may be any one of a number of suitable materials, including a titanium alloy such as Ti-6Al-4V, an aluminum alloy such as 7075-T6, alumina, aluminum nitride, zirconia, silicon carbide, silicone nitride, sapphire and ruby selected for one or more material properties, including, but not limited to speed of sound, thermal conductivity, ultrasonic power transmission efficiency, coefficient of friction and fatigue strength. Second portion 138 characteristically (wherein "characteristically" refers to the acoustic properties normally exhibited by the material) vibrates, for example, with a second wavelength when separately excited by the ultrasonic energy input. The second wavelength may be substantially greater than the first wavelength of first portion 136. An example of a second wavelength is approximately 174 mm.

First portion 136 and second portion 138 may be joined together using any one or a combination of a number of well-known processes, including but not limited to, brazing, fritting and mechanically coupling. When first portion 136 and second portion 138 are joined together and excited by the ultrasonic energy input, composite end effector 130 characteristically vibrates with a composite wavelength that is between the first and second wavelengths. For example, if the first wavelength of first portion 136 is approximately 87 mm and the second wavelength of second portion 138 is approximately 174 mm, a composite wavelength may fall in the range of approximately 87 to 174 mm. In addition to the materials used for first portion 38 and second portion 36, the exact magnitude of the composite wavelength may depend upon other factors, including physical configuration, mass proportion and distribution and the strength of the bond between first portion 136 and second portion 138.

Similarly, one or more of other material properties, including thermal conductivity, ultrasonic power transmission efficiency, coefficient of friction and fatigue strength of end effector 30 may have composite characteristic values, although not necessarily. Furthermore, each composite characteristic value associated with a material property may be in a range defined by the characteristic values for that material property of first portion 136 and second portion 138.

Composite end effector 130 may be configured such that its proximal end is near the most distal, vibrational nodal point 128 of waveguide 124, and such that the length of composite end effector 130 is approximately equal to a quarter of the composite wavelength. Therefore, the length of composite end effector 130 may be significantly longer than the length of a similarly configured and ultrasonically energized end effector made only of a single material such as a titanium alloy.

For the embodiments described herein, it has been assumed that the end effector vibrates primarily in the longitudinal direction in order to cut and coagulate tissue. However, it is possible for the end effector to vibrate primarily in any one or a combination of the following directions: longitudinal (along the z-axis), transverse (perpendicular to the z-axis), and torsional (about the z-axis) directions. It also should be noted that, although all the composite end effector embodiments shown in the figures herein are straight, it is also possible for the composite end effector to be curved or to have any one of numerous other configurations.

Although the composite end effector has been shown and described with respect to certain embodiments, it should be understood that modifications may occur to those skilled in the art. The composite end effector includes such modifications and is limited only by the scope of the claims.

What is claimed is:

1. A composite end effector for an ultrasonic surgical instrument comprising:
    a first portion formed from a first material selected from the group consisting of aluminum, aluminum alloy, titanium and titanium alloy, wherein said first material exhibits a first ultrasonic propagation wavelength when excited by an ultrasonic energy input; and
    a second portion formed from a second material selected from the group consisting of ceramic, alumina, sapphire, ruby, alumina nitride, zirconia, silicon carbide and silicon nitride, wherein said second material exhibits a second ultrasonic propagation wavelength when excited by said ultrasonic energy input;
    wherein said composite end effector exhibits a composite ultrasonic propagation wavelength that is between said first and second ultrasonic propagation wavelengths when excited by said ultrasonic energy input.

2. The composite end effector of claim 1 wherein a length of said composite end effector is approximately equal to one fourth of said composite ultrasonic propagation wavelength.

3. The composite end effector of claim 1 wherein said composite end effector vibrates in at least one of a longitudinal direction, a transverse direction and a torsional direction relative to a longitudinal axis of said composite end effector.

4. The composite end effector of claim 1 wherein said first portion includes a cavity that retains said second portion.

5. The composite end effector of claim 4 wherein said cavity is a longitudinal bore and said second portion substantially fills said bore.

6. The composite end effector of claim 1 wherein said first portion is connected to said second portion by at least one of a frit process, a braze process and a mechanical process.

7. The composite end effector of claim 1 wherein said second ultrasonic propagation wavelength is substantially greater than said first ultrasonic propagation wavelength.

8. The composite end effector of claim 1 wherein said second ultrasonic propagation wavelength is at least about 1.25 times said first ultrasonic propagation wavelength.

9. The composite end effector of claim 1 wherein said second ultrasonic propagation wavelength is at least about 1.5 times said first ultrasonic propagation wavelength.

10. The composite end effector of claim 1 wherein said second ultrasonic propagation wavelength is about 2 times said first ultrasonic propagation wavelength.

11. An ultrasonic surgical instrument comprising the composite end effector of claim 1 vibrationally coupled to an ultrasonic drive unit.

12. An ultrasonic transmission assembly comprising:
    a waveguide; and
    a composite end effector connected to said waveguide, said composite end effector including:
        a first portion formed from a metal or metal alloy that exhibits a first ultrasonic propagation wavelength when excited by an ultrasonic energy input; and
        a second portion formed from a second, non-metal material that exhibits a second ultrasonic propagation wavelength when excited by said ultrasonic energy input, said second ultrasonic propagation wavelength being at least about 1.25 times said first ultrasonic propagation wavelength,
    wherein said composite end effector exhibits a composite ultrasonic propagation wavelength that is between said first and said second ultrasonic propagation wavelengths when excited by said ultrasonic energy input, and
    wherein a length of said composite end effector is approximately equal to one fourth of said composite ultrasonic propagation wavelength.

13. The ultrasonic transmission assembly of claim 12 wherein said second ultrasonic propagation wavelength is at least about 1.5 times said first ultrasonic propagation wavelength.

14. The ultrasonic transmission assembly of claim 12 wherein said second ultrasonic propagation wavelength is at least about 2 times said first ultrasonic propagation wavelength.

15. A composite end effector for an ultrasonic surgical instrument comprising:
    a first portion formed from a metal or metal alloy, said first portion defining a cavity; and
    a second portion formed from a ceramic, sapphire or ruby, said second portion being received within said cavity,
    wherein said second portion is connected to said first portion such that said first and said second portions form a discontinuous interface therebetween, and
    wherein cracks formed in said second portion do not propagate into said first portion.

* * * * *